United States Patent
Yodfat et al.

(10) Patent No.: US 8,911,423 B2
(45) Date of Patent: Dec. 16, 2014

(54) SYSTEMS AND METHODS FOR GLYCEMIC CONTROL DURING PUMP DISCONNECTION

(75) Inventors: Ofer Yodfat, Maccabim-Reut (IL); Gali Shapira, Haifa (IL)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 953 days.

(21) Appl. No.: 12/170,936

(22) Filed: Jul. 10, 2008

(65) Prior Publication Data

US 2009/0048152 A1 Feb. 19, 2009

Related U.S. Application Data

(60) Provisional application No. 61/024,128, filed on Jan. 28, 2008, provisional application No. 60/959,552, filed on Jul. 12, 2007.

(51) Int. Cl.
- *A61M 31/00* (2006.01)
- *A61M 5/172* (2006.01)
- *A61M 5/142* (2006.01)

(52) U.S. Cl.
CPC ......... *A61M 5/1723* (2013.01); *A61M 5/14244* (2013.01); *A61M 2005/14208* (2013.01); *A61M 2230/201* (2013.01)
USPC ............................................ 604/504; 604/66

(58) Field of Classification Search
USPC ........................ 604/65–67, 504; 128/DIG. 13
See application file for complete search history.

(56) References Cited

U.S. PATENT DOCUMENTS

| | | | |
|---|---|---|---|
| 2002/0123740 A1* | 9/2002 | Flaherty et al. | 604/890.1 |
| 2003/0114836 A1 | 6/2003 | Estes et al. | 604/890.1 |
| 2007/0191702 A1 | 8/2007 | Yodfat et al. | |
| 2008/0172026 A1* | 7/2008 | Blomquist | 604/500 |
| 2008/0215035 A1 | 9/2008 | Yodfat et al. | |

FOREIGN PATENT DOCUMENTS

| | | |
|---|---|---|
| EP | 1 382 363 A1 | 1/2004 |
| WO | WO 2004/009161 A1 | 1/2004 |

OTHER PUBLICATIONS

International Search Report, date of mailing Dec. 2, 2008.
DCCT Trial, N. Engl J. Med 1993; 329: 977-986.
UKPDS Trial, Lancet 1998; 352: 837-853.
BMJ 1998; 317, (7160): 703-13.
EDIC Trial, N Engl J Med 2005; 353, (25): 2643-53.
International Search Report and Written Opinion of the International Search Authority for International Application No. PCT/IL2008/000950, date of mailing Dec. 2, 2008.
Allen et al., "Nocturnal Hypoglycemia: Clinical Manifestations and Therapeutic toward Prevention", *Endocrine Practice*, 9(6):530-543 (2003).

(Continued)

*Primary Examiner* — Manuel Mendez
(74) *Attorney, Agent, or Firm* — Roche Diagnostics Operations, Inc.

(57) ABSTRACT

Techniques and devices are described for allowing a diabetes patient to safely disconnect an insulin infusion system device for a time period. In one aspect, the techniques and devices can be implemented by receiving a maximum glucose amount, a minimum glucose amount, and a contemplated disconnection time; receiving a current glucose amount of the user; determining an expected increase in glucose of the user based on the contemplated disconnection time, an insulin sensitivity of the user and a contemplated basal insulin dose; validating the contemplated disconnection time based on at least one of the expected increase in glucose, the maximum glucose amount, and the minimum glucose amount; and, administering a therapeutic action to the user based on the validation of the contemplated disconnection time.

28 Claims, 16 Drawing Sheets

(56) References Cited

OTHER PUBLICATIONS

DCCT Trial Research Group, "The Effect of Intensive Treatment of Diabetes on the Development and Progression of Long-Term Complications in Insulin-Dependent Diabetes Mellitus", *N. E. J. Med.,* 329:977-986 (1993).

Nathan et al., "Intensive Diabetes Treatment and Cardiovascular Disease in Patients with Type 1 Diabetes", *N.E. J. Med.,* 353(25):2643-2653 (2005).

Perriello et al., "The Effect of Asymptomatic Nocturnal Hypoglycemia on Glycemic Control in Diabetes Mellitus", *N. E. J. Med.,* 319:1233-1239 (1988).

Schiffrin et al., "Predicting nocturnal hypoglycemia ni patients with type I diabetes treated with continuous subcutaneous insulin infusion", *Am. J. Med.,* 82(6):1127-1132 (1987).

UKPDS Group Trial, "Tight blood pressure control and risk of macrovascular and microvascular complications in type 2 diabetes: UKPDS 38", *BMJ,* 317:703-713 (1998).

UKPDS Trial, "Intensive blood-glucose control with sulphonylureas or insulin compared with conventional treatment and risk of complications in patients with type 2 diabetes (UKPDS 33)", Lancet, 352:837-853 (1998).

\* cited by examiner

SYSTEMS AND METHODS FOR GLYCEMIC CONTROL DURING PUMP DISCONNECTION

RELATED APPLICATIONS

This application claims priority to U.S. Provisional Application Ser. No. 60/959,552 filed Jul. 12, 2007, which is herein incorporated by reference in its entirety. This application also claims priority to U.S. Provisional Application Ser. No. 61/024,128 filed Jan. 28, 2008 which is herein incorporated by reference in its entirety.

FIELD OF THE INVENTION

Techniques and devices are described relating to sustained medical infusion of therapeutic fluids for patients. In particular, techniques and devices are described for allowing a diabetes patient to safely disconnect an insulin infusion system device for a predetermined period of time.

BACKGROUND

Diabetes mellitus is a disease of major global importance, increasing in frequency at almost epidemic rates, such that the worldwide prevalence in 2006 is 170 million people and predicted to at least double over the next 10-15 years. Diabetes is characterized by a chronically raised blood glucose concentration (hyperglycemia), due to a relative or absolute lack of the pancreatic hormone, insulin. Within the healthy pancreas, beta cells, located in the islets of Langerhans, continuously produce and secrete insulin according to the blood glucose levels, maintaining near constant glucose levels in the body.

Much of the burden of the disease to the user and to health care resources is due to the long-term tissue complications, which affect both the small blood vessels (microangiopathy, causing eye, kidney and nerve damage) and the large blood vessels (causing accelerated atherosclerosis, with increased rates of coronary heart disease, peripheral vascular disease and stroke). The Diabetes Control and Complications Trial (DCCT) demonstrated that development and progression of the chronic complications of diabetes are greatly related to the degree of altered glycemia as quantified by determinations of glycohemoglobin (HbAlc). [DCCT Trial, N Engl J Med 1993; 329: 977-986, UKPDS Trial, Lancet 1998; 352: 837-853. BMJ 1998; 317, (7160): 703-13 and the EDIC Trial, N Engl J Med 2005; 353, (25): 2643-53]. Thus, maintaining normolycemia by frequent glucose measurements and adjustment of insulin delivery accordingly is of utmost importance.

Insulin pumps deliver rapid acting insulin 24 hours a day through a catheter placed under the skin. The total daily insulin dose is divided into basal and bolus doses. Insulin bolus doses are delivered before or after meals to counteract carbohydrates loads or during episodes of high blood glucose levels (correction boluses "CB"). The amount of insulin in the administered bolus depends on several parameters:

Amount of carbohydrates (Carbs) to be consumed
Carbohydrate-to-insulin ratio (CIR), i.e. the amount of carbohydrates balanced by one unit of insulin
Insulin sensitivity (IS), i.e. the amount of blood glucose level lowered by one unit of insulin.
Current blood glucose level
Target blood glucose (TBG) level (i.e. the desired blood glucose level). TBG for most diabetes patients is in the range of 90-130 mg/dL before a meal, and less than 180 mg/dL 1-2 hours after the beginning of a meal.
Residual insulin (RI), i.e. the amount of stored insulin remained in the body after recent bolus delivery that is still active. This parameter is relevant when there is a short time interval between consecutive bolus doses (e.g. less than 5 hours).

Basal insulin can be delivered continuously over 24 hours, and can keep the blood glucose concentration levels (namely, blood glucose levels) in normal desirable range between meals and overnight. Diurnal basal rates can be pre-programmed or manually changed according to various daily activities. Although basal delivery should be continuously administered it is often interrupted due to periodic pump disconnection. These interruptions can hamper glycemic control and if prolonged can cause life threatening ketoacidosis (DKA).

SUMMARY OF THE INVENTION

Techniques and devices are described for allowing a diabetes patient to safely disconnect an insulin infusion system device for a time period. In one aspect, the insulin infusion system can be implemented using a glucose measurement device adapted to measure a current amount of glucose in a user's body. In one variation, the insulin infusion system can also be implemented using a controlled disconnection apparatus adapted to determine an amount of insulin for dispensing into the user's body, such that the amount of insulin being determined as a function of the current amount of glucose and a contemplated disconnection time. The insulin infusion system can also be implemented using an insulin infusion pump adapted to dispense the determined amount of insulin into the user.

In one variation, the glucose measurement device can dispense insulin and implement a method for the controlled disconnection of the infusion device. The infusion device can be implemented as a miniature skin securable patch that can continuously dispense insulin, and that can also implement a method for the controlled disconnection of the infusion device. In some variations, the insulin infusion patch can be controlled remotely and can employ a method for controlled disconnection of the infusion device. The infusion device can also continuously monitor the body glucose concentration levels (e.g. blood glucose, ISF glucose).

In another variation, a semi-closed-loop system can be provided that can monitor the glucose levels, dispense insulin according to sensed glucose levels, and employ a method for controlled disconnection of the infusion device. This system can be implemented in a miniature single device that is discrete and economical for the users and highly cost effective for the payer.

In some variations, a device can be provided that comprises an insulin patch unit with a disposable part and a reusable part. The reusable part can include all relatively expensive components and the disposable part can include relatively inexpensive components. The device can also employ a method for the controlled disconnection of the infusion device.

In another aspect a system and a method can be implemented by receiving a maximum glucose amount, a minimum glucose amount, and a contemplated disconnection time; receiving a residual insulin amount of a user and a current glucose amount of the user; determining an expected increase in glucose of the user based on the contemplated disconnection time, an insulin sensitivity of the user and a contemplated basal insulin dose; validating the contemplated disconnection time based on at least one of the expected increase in glucose, the maximum glucose amount, and the minimum glucose amount; administering a therapeutic action to the user based on the validation of the contemplated disconnection time.

In one variation, the therapeutic action comprises displaying a message corresponding to the validation of the contemplated time to the user. In another variation the therapeutic action comprises advising the user to administer a disconnection bolus. In another variation the therapeutic action comprises advising the user to limit the contemplated disconnection time. In another variation, the therapeutic action comprises advising the user to administer a reconnection bolus.

In another aspect, a method for controlled disconnection can be provided. In one variation, the method comprises measuring a current amount of glucose in a user's body using a glucose measuring device; determining an amount of insulin for dispensing into the user's body as a function of the current amount of glucose and a contemplated disconnection time; and, dispensing the determined amount of insulin into the user.

In one variation, the amount of insulin can be determined based on an input selected from the group consisting of the insulin sensitivity, a target glucose level, an amount of residual insulin, the maximum glucose amount and the minimum glucose amount, a portion of a bolus in progress. In one implementation, the method for controlled disconnection further comprises continuously monitoring the current amount of glucose in the user's body. In one implementation, the contemplated disconnection time can be configurable by the user.

In one implementation, the dispensing the determined amount of insulin into the user is performed prior to a disconnection. In another implementation, the dispensing the determined amount of insulin into the user is performed after a reconnection. In another implementation, a first portion of the bolus amount is dispensed into the user prior to a disconnection and a second portion of the bolus amount is dispensed into the user after a reconnection.

Articles are also described that comprise a machine-readable medium embodying instructions that when performed by one or more machines result in operations described herein. Similarly, computer systems are also described that may include a processor and a memory coupled to the processor. The memory may encode one or more programs that cause the processor to perform one or more of the operations described herein.

In another aspect, an insulin device disconnection system is described. In one implementation the system comprises means for determining a current amount of glucose in a user's body; means for determining a current amount of insulin in the user's body; means for validating a contemplated disconnection time as a function of the current amount of glucose and the current amount of insulin; a processor adapted for determining an amount of insulin for dispensing into the user's body corresponding to the validation of the contemplated disconnection time; and, an insulin infusion pump adapted for dispensing the determined amount of insulin into the user.

In one variation, the insulin device disconnection system further comprises means for displaying a message corresponding to the validation of the contemplated disconnection time to the user. In another variation, the system further comprises means for advising the user to administer a disconnection bolus. In yet another variation, the system further comprises means for advising the user to limit the contemplated disconnection time. In another variation, the system further comprises means for advising the user to administer a reconnection bolus.

The details of one or more variations of the subject matter described herein are set forth in the accompanying drawings and the description below. Other features and advantages of the subject matter described herein will be apparent from the description and drawings, and from the claims.

DETAILED DESCRIPTION

Figure 1A:
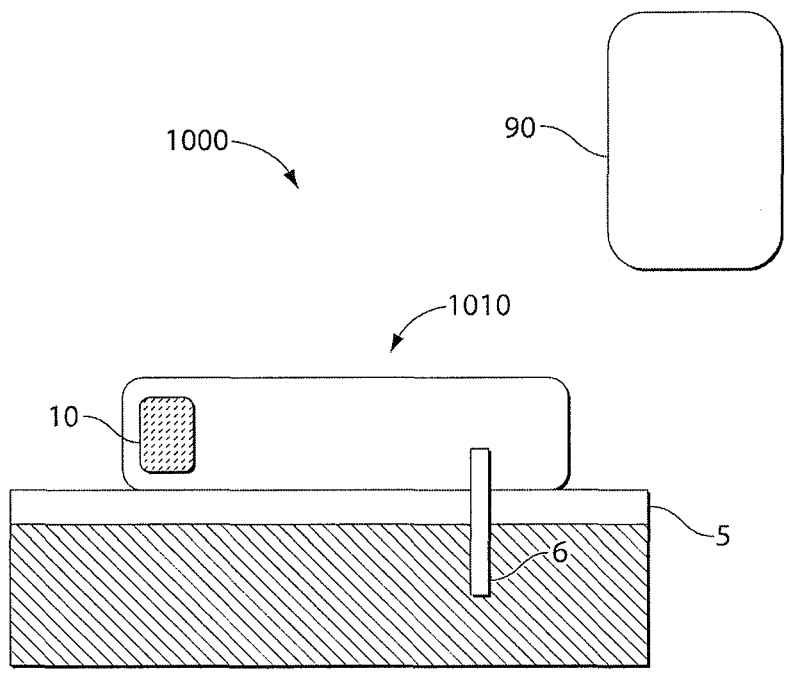
FIGS. 1a-b illustrate two configurations of an insulin infusion system comprising an insulin infusion pump, a glucose measurement device, and a controlled disconnection apparatus.

Techniques and devices are described for allowing a diabetes patient to safely disconnect an insulin infusion system device for a time period. In one aspect, the insulin infusion system can be implemented using a glucose measurement device adapted to measure a current amount of glucose in a user's body. In one variation, the insulin infusion system can also be implemented using a controlled disconnection apparatus adapted to determine an amount of insulin for dispensing into the user's body, such that the amount of insulin being determined as a function of the current amount of glucose and a contemplated disconnection time.

In another aspect a system and a method for controlled disconnection can be implemented by receiving a maximum blood glucose amount, a minimum blood glucose amount, and a contemplated disconnection time; receiving a residual insulin amount of a user and a current blood glucose amount of the user; determining an expected increase in blood glucose of the user based on the contemplated disconnection time, an insulin sensitivity of the user and a contemplated basal insulin dose; validating the contemplated disconnection time based on at least one of the expected increase in blood glucose, the maximum blood glucose amount, and the minimum blood glucose amount; administering a therapeutic action to the user based on the validation of the contemplated disconnection time.

In some implementations, the method for controlled disconnection of the infusion device can be conducted according to one or more of the following actions, which can be performed in the order presented or in any other suitable order.

In some implementations, a user or another party (e.g., physician) may set a maximum tolerable blood glucose (BG) level (e.g. 150 mg/dL) and a minimal tolerable BG level (e.g.

60 mg/dL). Prior to disconnection, the user may check if there is a bolus in process, current BG (CBG) and, and user's residual insulin (RI). In some embodiments, the actions described above can be carried out automatically, without any intervention from the user or another party. For example, a check for the current blood glucose level, can be carried out by a continuous glucose monitor (CGM).

The user can also select a contemplated basal insulin dose (basal) that would have been administered had there been no contemplated pump disconnection. The user may choose not to change his/her basal or choose an alternative basal. For example, if intensive physical activity is contemplated during the disconnection time a lower basal rate can be selected. Alternatively, the user can choose an activity level and the basal rate can be modified accordingly. In such a case, initial settings that correlate between activity level and basal insulin rate can be mandatory.

The user can also input into the system a contemplated disconnection time (T). Feasibility of disconnection duration can be tested by the device, based on the specific parameters of the user. If the contemplated disconnection time is too long, the device can offer a disconnection bolus that can lower the BG. In some implementation the offered disconnection bolus cannot bring the blood glucose BG below the minimal tolerable blood glucose $BG_{min}$ The lowered BG can allow a longer duration of disconnection. For example, the disconnection boluses (DB) may be calculated according to the following equations:

a. If there is no bolus in process and no residual insulin then $$DB=((CBG+BG_{ei}-BG_{max})/IS)$$

b. If there is no bolus in process and there is residual insulin then $$DB=((CBG+BG_{ei}-BG_{max})/IS)-RI$$

c. If there is a bolus in process (residual bolus–REB) then $$DB=((CBG+BG_{ei}-BG_{max})/IS)+REB$$

2. A second feasibility test can automatically be conducted. If the contemplated disconnection time is still too long, despite lowering the BG, a time limit will be offered.
3. The time limit can be calculated according to the following equations:
    a. If there is no bolus in process and no residual insulin then $$T_{max}=(BG_{max}-BG_{min})/(basal*IS)$$

The disconnection bolus in such a case is:

$$DB=((CBG-BG_{min})/IS)$$

b. If there is no bolus in process and there is residual insulin then $$T_{max}=(BG_{max}-BG_{min}+RI*IS)/(basal*IS)$$

The disconnection bolus in such a case is:

$$DB=((CBG-BG_{min})/IS)-RI$$

c. If there is a bolus in process (residual bolus–REB) then $$T_{max}=(BG_{max}-BG_{min}-REB*IS)/(basal*IS)$$

The disconnection bolus in such a case is:

$$DB=((CBG-BG_{min})/IS)+REB$$

In some implementations, after reconnection of the pump, a reconnection bolus (RB) can also be administered to bring the user back to target blood glucose levels (TBG). For example, if the user's disconnection time was limited by the device, a correction bolus can be administered automatically with or without user interface according to the following equation:

$$RB=(BGmax-TBG)/IS.$$

If the user's disconnection time was not limited by the device, and there was no need for a disconnection bolus, a correction bolus may automatically be administered, for example, according to the following equations:
    i. If no bolus in process and no RI:
        RB=(CBG+basal*T*IS−TBG)/IS for a constant basal rate. For an inconstant basal rate the correction bolus is as follows:

$$RB=(CBG+\Sigma basal_x*t_x*IS-TBG)/IS$$

ii. If no bolus in process and RI>0:
        RB=(CBG+basal*T*IS−TBG)/IS−ΣRI for a constant basal rate. For an inconstant basal rate the correction bolus is as follows:

$$RB=(CBG+\Sigma basal_x*t_x*IS-TBG)/IS-\Sigma RI$$

iii. If a bolus in process:
        RB=(CBG+Σbasal*T*IS−TBG)/IS+REB for a constant basal rate. For an inconstant basal rate the correction bolus is as follows:

$$RB=(CBG+\Sigma basal_x*t_x*IS-TBG)/IS+REB$$

d. If the user's disconnection time was not limited by the device, and there was a need for a disconnection bolus, a correction bolus may automatically be administered according to the following equation:
    iv. If no bolus in process and no RI:
        RB=(CBG−DB*IS+basal*T*IS−TBG)/IS for a constant basal rate. For an inconstant basal rate the correction bolus is as follows:

$$RB=(CBG-DB*IS+\Sigma basal_x*t_x*IS-TBG)/IS$$

v. If no bolus in process and RI>0:
        RB=(CBG−DB*IS+basal*T*IS−TBG)/IS−ΣRI for a constant basal rate. For an inconstant basal rate the correction bolus is as follows:

$$RB=(CBG-DB*IS+\Sigma basal_x*t_x*IS-TBG)/IS-\Sigma RI$$

vi. If a bolus in process:
        RB=(CBG−DB*IS+basal*T*IS−TBG)/IS+REB for a constant basal rate. For an inconstant basal rate the correction bolus is as follows:

$$RB=(CBG-DB*IS+\Sigma basal_x*t_x*IS-TBG)/IS+REB$$

Alternatively, the user can check his/her reconnection blood glucose level (RBG), and a correction bolus is administered according to the following equation:

$$RB=(RBG-TBG)/IS$$

In some variations, the user can indicate that a disconnection is desired, without providing a specific desired disconnection time. The device can then display the maximum feasible disconnection time. In some implementations, the user can also be advised to avoid food intake during the time disconnected from the infusion device.

In some variations, the time needed for significant absorption of insulin after reconnection can also be considered (e.g. 20 minutes). This absorption time (tabs) may be constant. For example, the basic feasibility equation when considering tabs can be as follows:

$$BGmax>CBG+basal*(T+tabs)*IS$$

The maximum feasible disconnection time is therefore as follows:

$$t = ((BGmax - BGmin)/(basal*IS)) - tabs$$

According to one implementation, the tabs can be user specific based on one or more individual parameters such as BMI (higher BMI→higher tabs), fat percentage, sex, and age.

A reconnection alarm can also be installed in the remote control unit of the device. It can remind the user to reconnect a few minutes (e.g. 5 minutes) prior to and/or at the contemplated disconnection time or the disconnection time limit.

The device can also be implemented using a sensing apparatus that recognizes/determines when disconnection and reconnection occurs. In some implementations, the sensing apparatus can be located in the reusable part of the patch unit of the device. The controlled disconnection method can also be implemented in the insulin infusion device. The controlled disconnection method can be implemented in a device which can deliver insulin and monitor glucose, where the insulin can be delivered automatically or semi-automatically according to sensed glucose levels (closed, semi closed or open loop system).

In still other implementations, the controlled disconnection method can be implemented in an insulin infusion device comprising an insulin dispensing patch unit and a remote control unit, wherein a glucose sensing apparatus (e.g. glucometer) is integrated in the remote control unit. In one such implementation, the dispensing patch unit may be composed of two parts: a reusable part that includes all electronic and driving elements (i.e. relatively expensive elements) and a disposable part that includes insulin reservoir and other inexpensive elements. The glucose sensing apparatus (e.g. glucometer) can alternatively be integrated in the reusable part of the infusion patch unit of the device.

In some implementations, the controlled disconnection method can be implemented in the remote control unit of the insulin infusion device. Alternatively, the controlled disconnection method can be implemented in the reusable part of the dispensing patch unit of the device. The insulin dispensing and glucose sensing capabilities can be implemented using an open loop, or semi closed loop systems. In a closed loop mode, an analyte concentration is sensed by a sensor and determined by a processor and the processor commands a dispensing apparatus to dispense one or more therapeutic fluids to the human body based on the determined concentration. In an open loop mode, the sensing and dispensing functions are not linked. A device operating in this mode can indicate a value for the determined analyte concentration, but no feedback control is exercised over the rate of dispensing. A user interface or other means by which a user can communicate commands to the device can allow the user to dispense the therapeutic fluid. In the semi-closed mode, the sensing occurs as noted above for the closed loop mode. However, the device can wait for confirmation or alternatively it can request such confirmation, possibly via some user interface, from a user before dispensing the therapeutic fluid in the amounts that might be needed based on the determined analyte concentration.

The controlled disconnection method can be implemented in the remote control unit of the device. Alternatively, the method could be implemented in the reusable part of dispensing patch unit of the device. Alternatively, the method could be implemented in both the reusable part of the dispensing patch unit of the device and the remote control unit of the device.

Figure 1B:
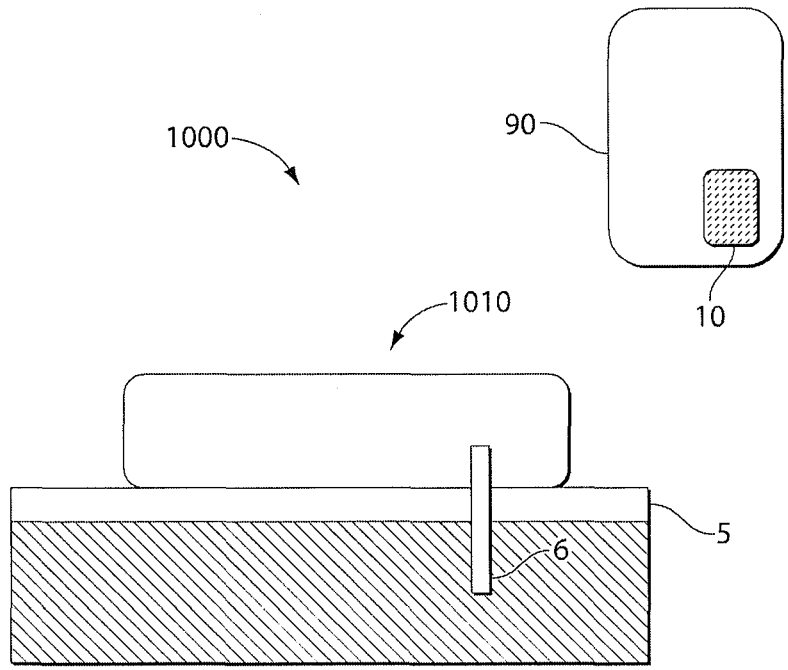

FIGS. 1a-b show a system 1000 comprising an insulin infusion pump 1010, a glucose measurement device (e.g. glucometer) 90, and a controlled disconnection apparatus 10. The controlled disconnection apparatus 10 can include any suitable hardware, software, or combination thereof. The insulin infusion pump 1010 can comprise a cannula 6 that can penetrate the skin 5 to allow delivery of insulin.

In FIG. 1a, the controlled disconnection apparatus 10 is located in the insulin infusion pump 1010. In FIG. 1b, the controlled disconnection apparatus 10 is located in the glucose measurement device 90. The insulin infusion pump 1010 can communicate with a remote control unit (not shown in the figures) allowing programming, user inputs and data acquisition. The controlled disconnection apparatus can be installed in the remote control unit.

The insulin infusion pump can include a glucometer. The glucometer can be installed in the remote control unit of the pump or in the pump unit itself. The controlled disconnection apparatus can be located in the glucometer, pump unit, or the remote control unit. The insulin infusion system can comprise an insulin infusion pump, a continuous glucose measurement (CGM) device, and a controlled disconnection apparatus. The controlled disconnection apparatus can be located in either the pump or the CGM device.

The insulin infusion pump can comprise a continuous glucose measurement (CGM) device. The infusion pump and continuous glucose measurement (CGM) device can be located in the same housing and can communicate with a remote control unit. A controlled disconnection apparatus can be located in the CGM and pump unit, or in the remote control unit.

Figure 2A:
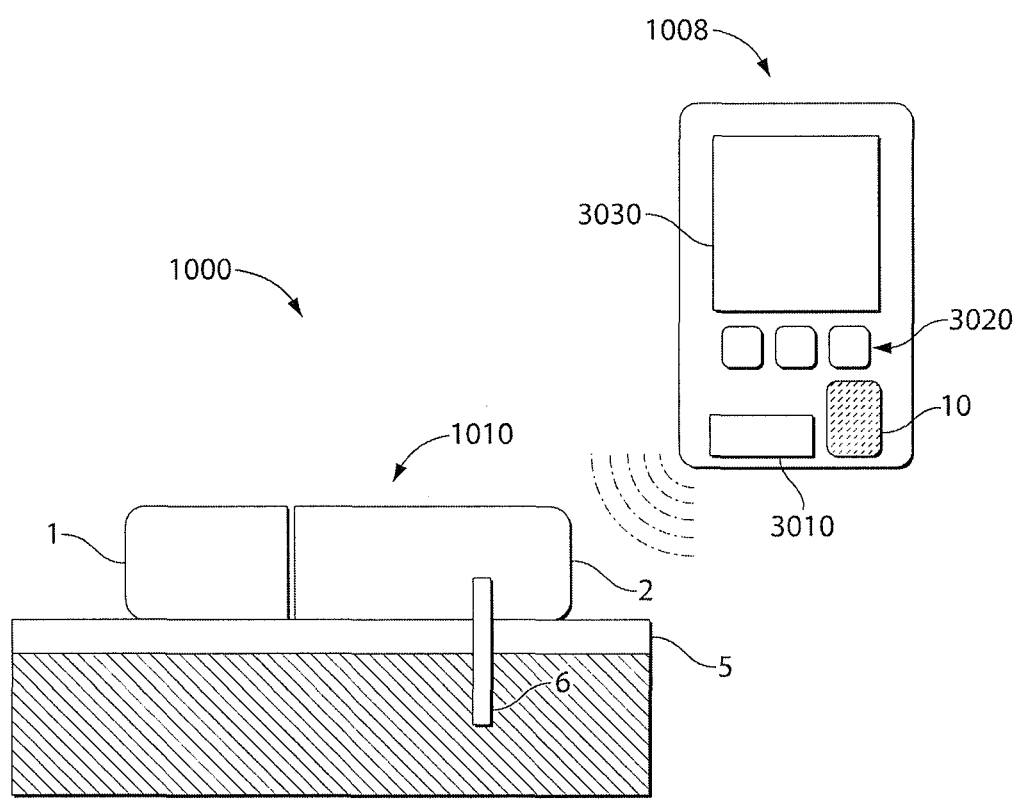
FIGS. 2a-b illustrate two configurations of an insulin infusion system comprising an insulin dispensing unit and a remote control unit that includes a controlled disconnection apparatus.
Figure 2B:
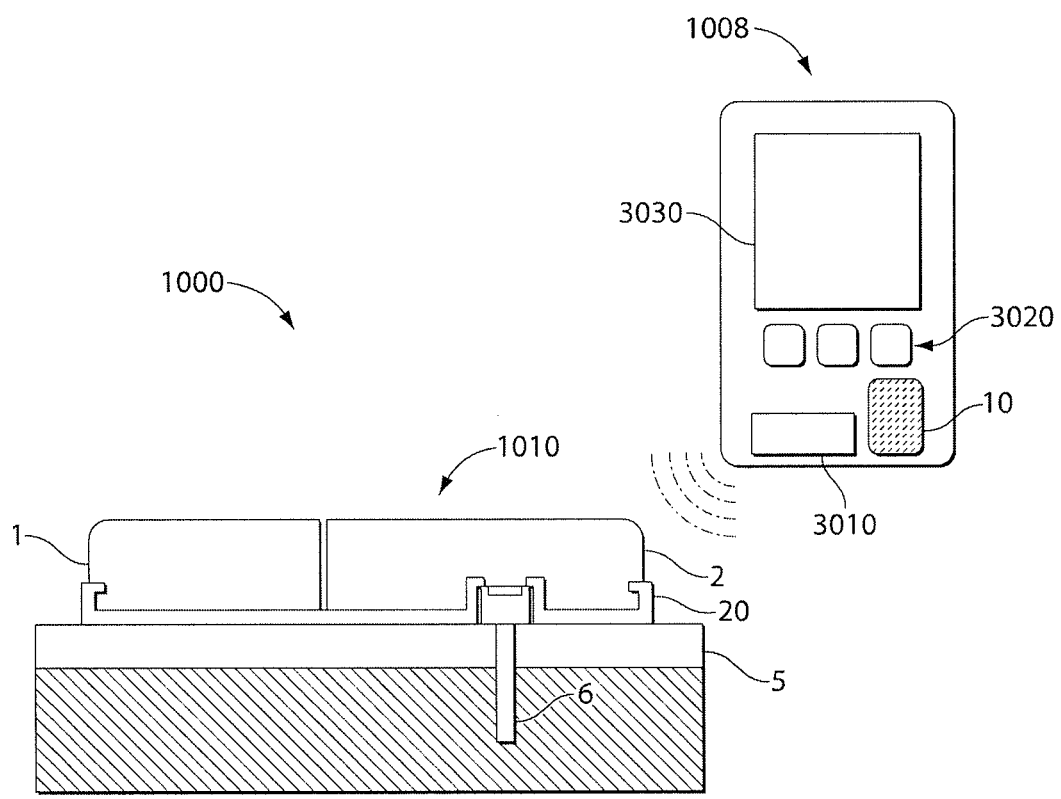

FIGS. 2a-b show an insulin infusion system, in which an insulin infusion device 1010 can be configured as a patch unit, which can be adhered to the user's skin 5. The system can comprise a remote control unit 1008, which can communicate with the patch unit, allowing programming, user inputs and data acquisition.

Manual inputs can be effected by buttons (not shown in FIG. 2a-b) that can be located on the patch unit. The patch unit can be configured to include one part in one housing as shown in FIG. 2a. Alternatively, the patch unit can be configured to include two parts—a reusable part 1 and a disposable part 2, as shown in FIG. 2b.

The patch unit can be configured to include a cannula 6 that can penetrate the skin 5 to allow delivery of insulin to the patient. The patch unit 1010 can be attached to a dedicated cradle unit 20 that can be a flat sheet adhered to the user's skin 5 and can allow connection/disconnection of the patch unit 1010. An example of this configuration is discussed in a co-owned, co-pending U.S. Provisional Patent Application No. 60/876,679, incorporated in its entirety hereto by reference.

The remote control unit 1008 can contain the controlled disconnection apparatus 10. The disconnection apparatus 10 can include a processor 3010, input means 3020 and a display 3030. The input means can be used for the controlled disconnection apparatus 10 and for the patch unit 1010 programming. The control unit 1008 can contain additional indication means e.g. audible, vibrational, etc.

Figure 3A:
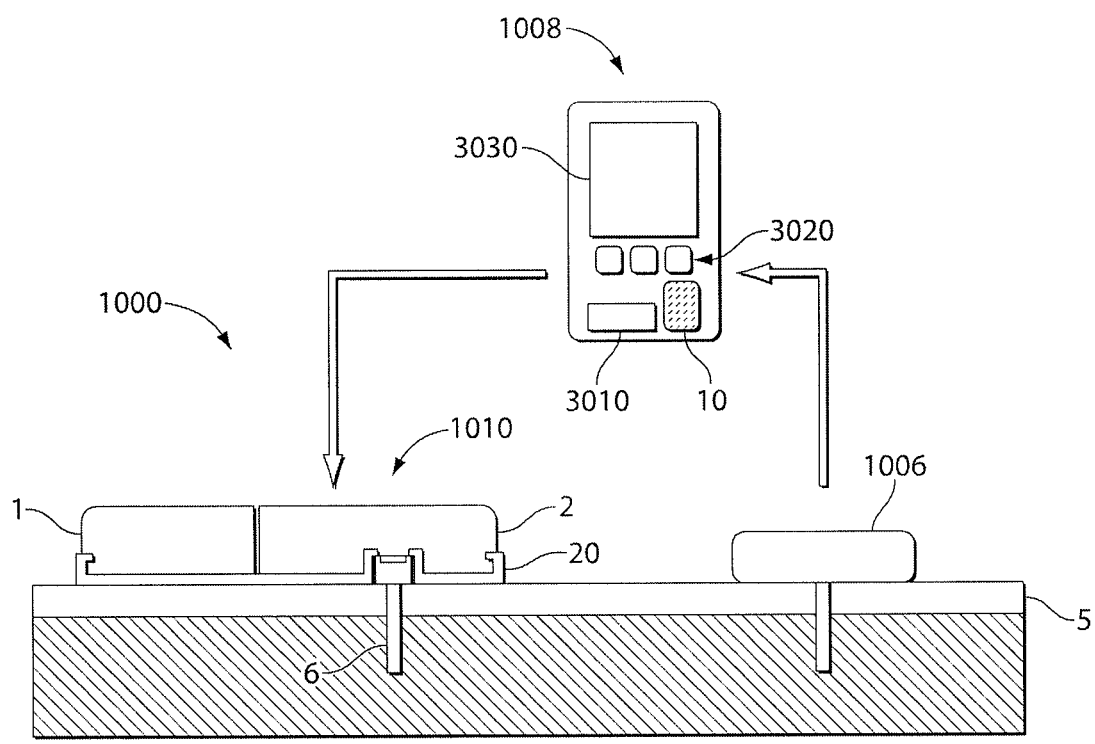
FIGS. 3a-b illustrate two configurations of an insulin infusion device comprising a continuous subcutaneous glucose monitors providing blood glucose readings (BG) for the controlled disconnection apparatus.
Figure 3B:
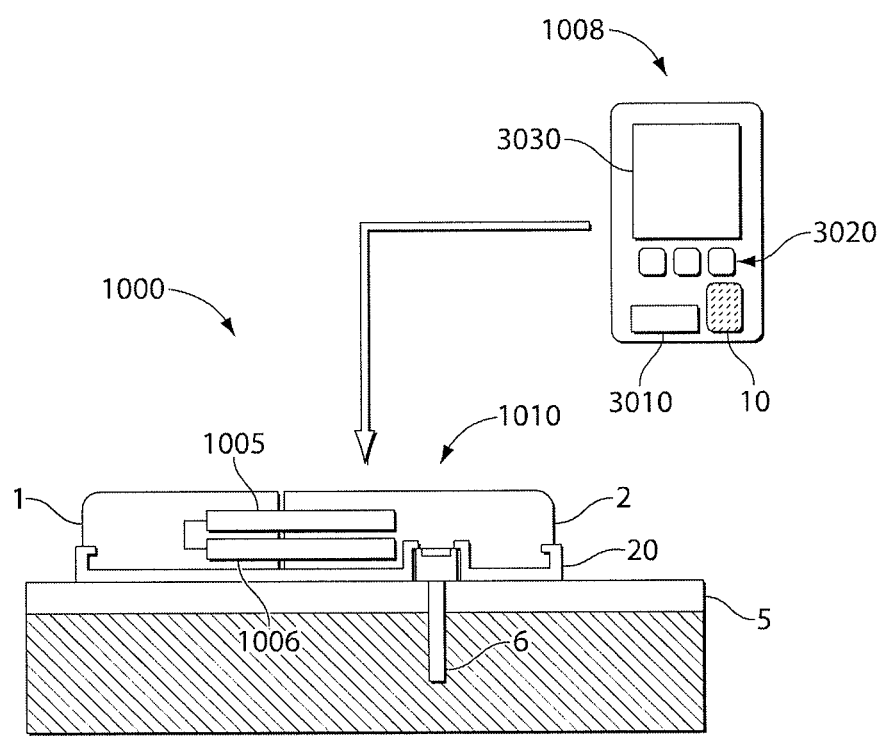

FIGS. 3a-b illustrate another implementation of the insulin infusion system 1000, in which blood glucose readings, used by the controlled disconnection apparatus 10 can be received from a continuous subcutaneous glucose monitor 1006. A communication channel between the continuous subcutaneous glucose monitor 1006 and the controlled disconnection apparatus 10 residing in the remote control unit 1008 can be maintained for programming, data handling and user input purposes.

FIG. 3a illustrates an insulin infusion system 1000, in which the current blood glucose (CBG) is measured by an independent continuous subcutaneous glucose monitor 1006. FIG. 3b illustrates an insulin infusion system 1000, in which the continuous subcutaneous glucose sensing (monitoring) apparatus 1006 can be integrated within the patch unit 1010 of the insulin delivery device.

The insulin dispensing apparatus 1005 and glucose sensing apparatus 1006 can constitute a single delivery device, and can use a single cannula 6 for both dispensing and sensing as described in detail in our previous U.S. application Ser. No. 11/706,606, filed Feb. 14, 2007, incorporated herein by reference in its entirety.

The sensing apparatus and the dispensing apparatus can have separate cannulae that can penetrate the skin 5 and reside in the subcutaneous tissue. The delivery device of this implementation can be comprised of two parts—a reusable part 1 and a disposable part 2, each part has corresponding housing 1001, 1002. In some implementations, the patch unit 1010 can be attached to a dedicated cradle unit 20 adhered to the user's skin 5. The dedicated cradle unit 20 can allow connection/disconnection of the patch unit 1010.

Figures 1, 4:
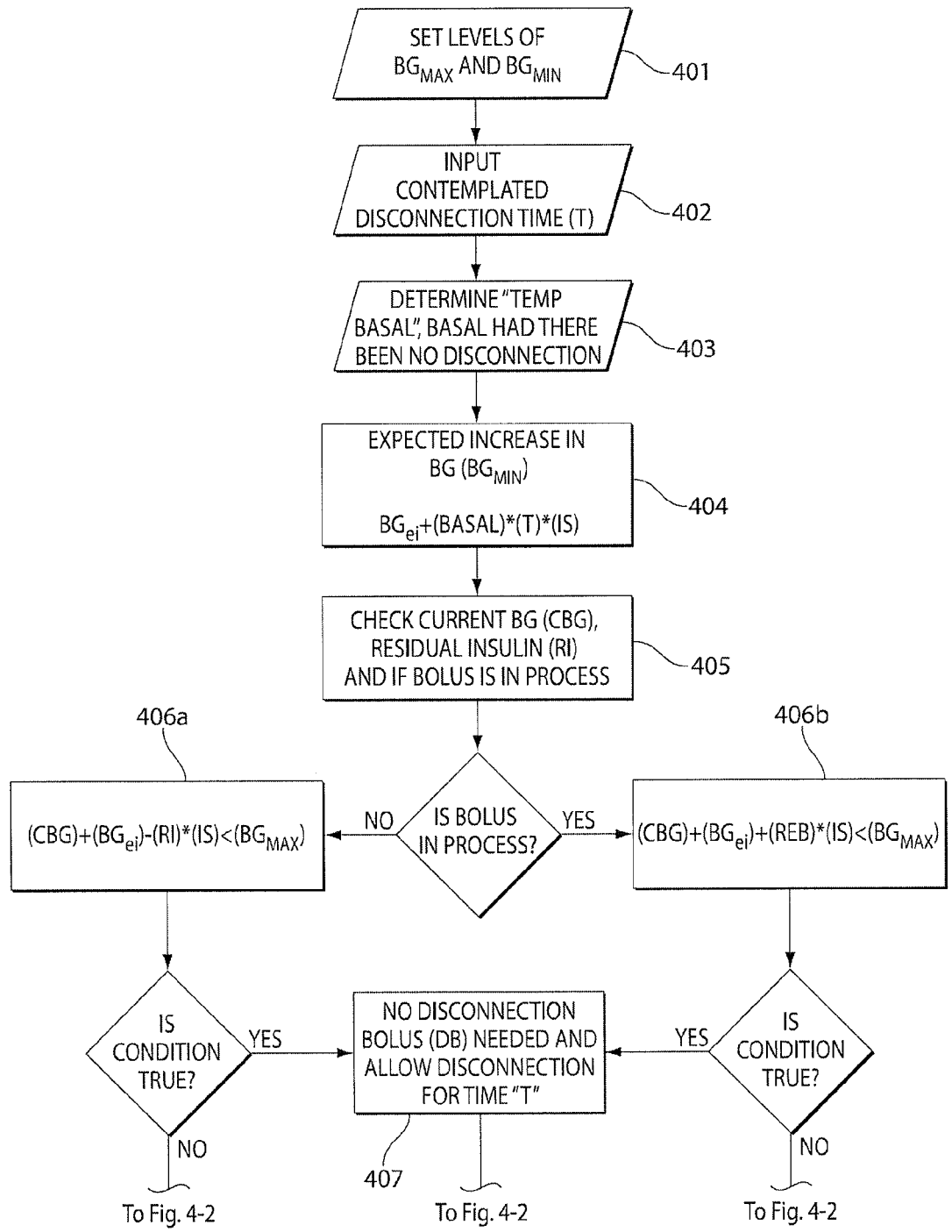
FIG. 4 is a block diagram illustrating a controlled disconnection method.
Figures 2, 4:
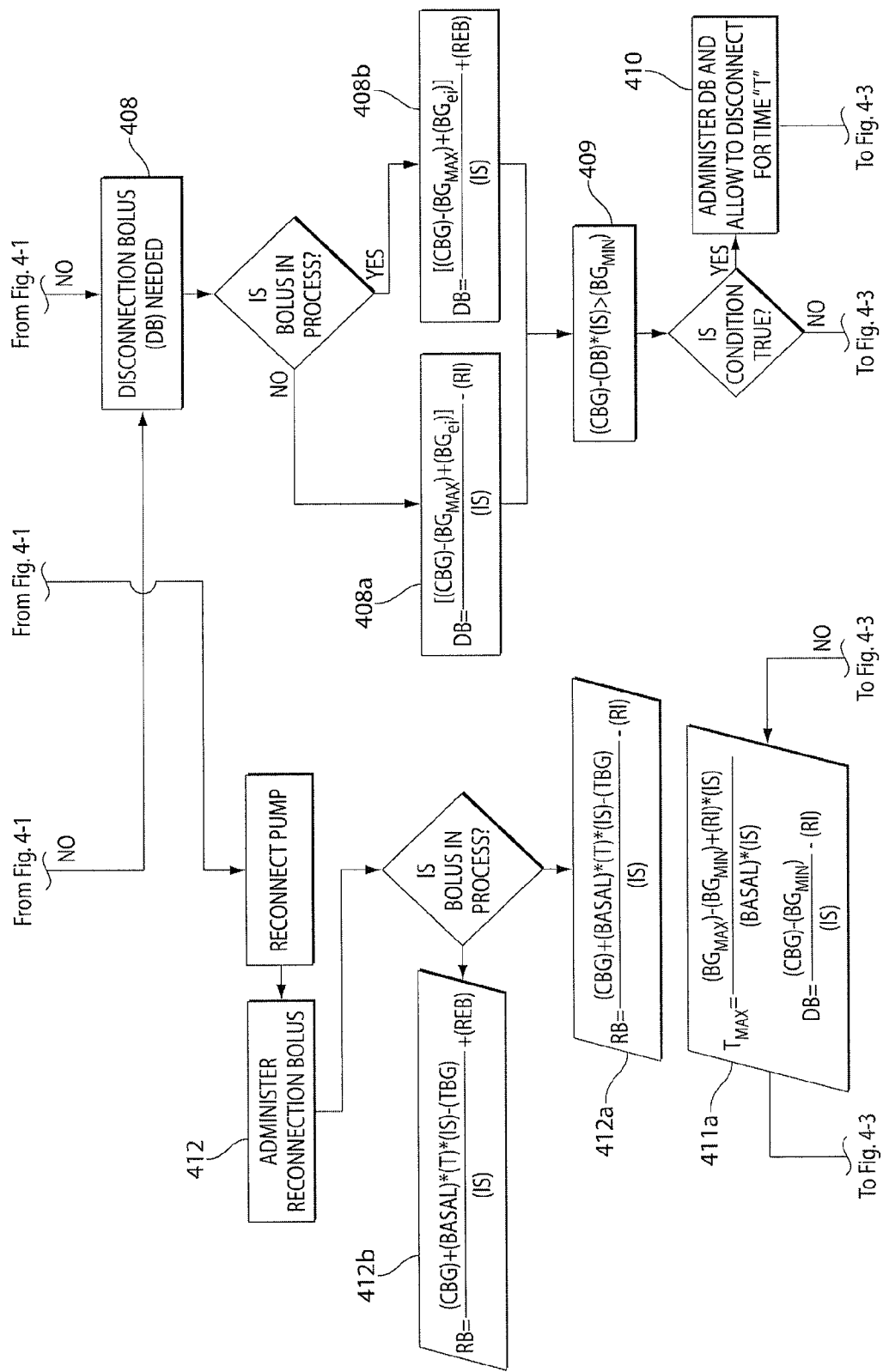
Figures 3, 4:
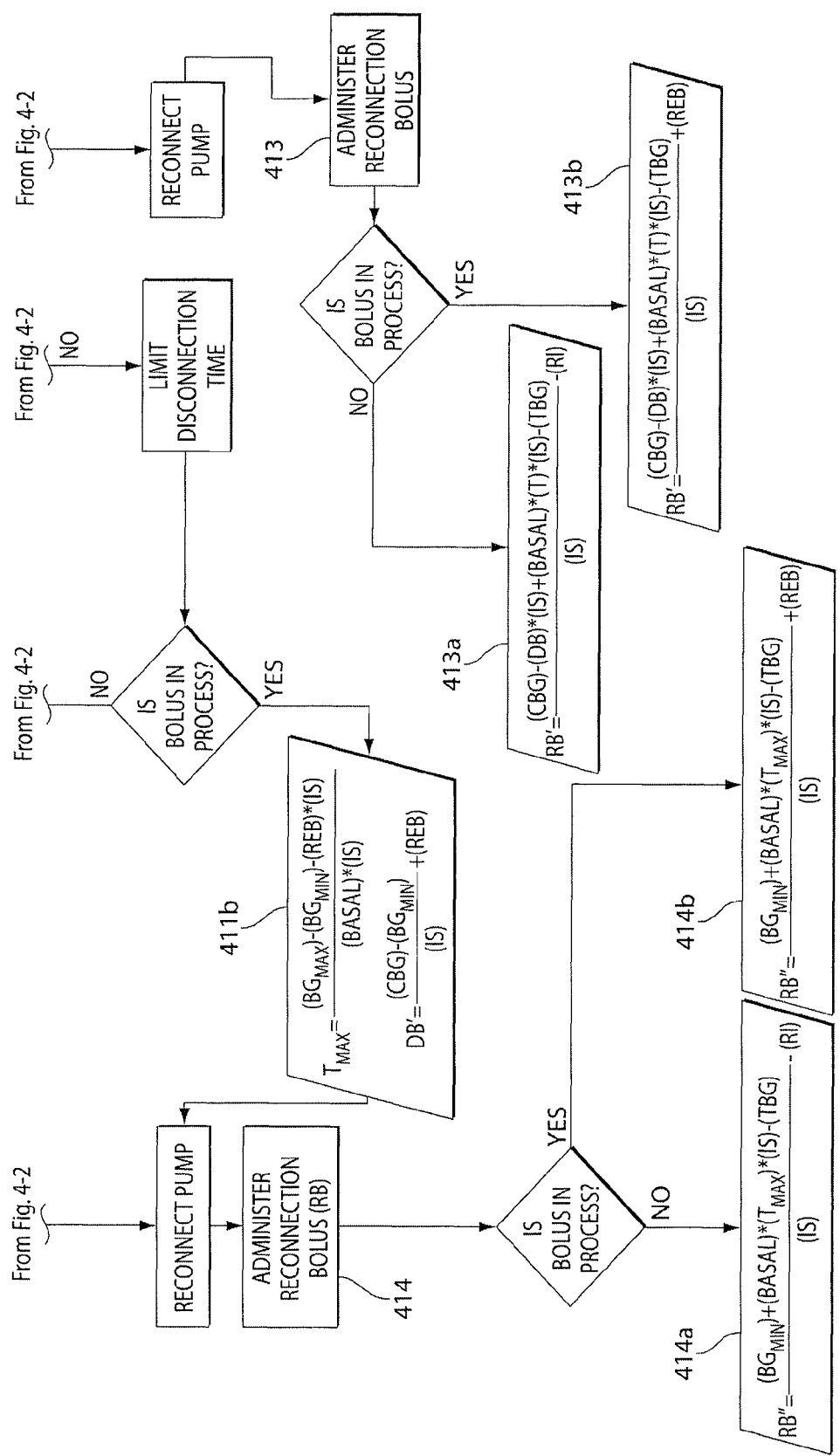

FIG. 4 illustrates a block diagram according to one implementation of a controlled disconnection method. At 401, the user or another party (e.g., physician) can set a maximum tolerable BG level (BGmax), e.g. 150 mg/dL, and a minimal tolerable BG level (BGmin), e.g. 60 mg/dL. In some implementations, BGmax and/or BGmin can be preprogrammed into the apparatus. At 402, the user can input the desired disconnection time, "T". At 403, the user can input the basal rate that would have been delivered had there been no disconnection. At 404, the device can calculate the increase in BG that is expected if the user disconnects, according to the desired disconnection time "T" from step 402 and the basal rate set at step 403.

In some implementations, the expected increase in BG (BGei) can be calculated according to the following equation:

$$BGei = basal * T * IS$$

If the basal rate is inconstant, than BGei can be calculated as a summation of each basal rate multiplied by the time to be spent at the basal rate multiplied by IS. The total time equals "T". That is, BGei=Σbasalx*tx*IS, as elaborated later in the description.

At 405, the current blood glucose level (CBG) can be measured. This can be carried out automatically if the device comprises a CGM. The user can also check if there is a bolus in process and if there is any residual insulin (RI) (these parameters can also be automatically obtained without the user interface). At 406a or 406b, the feasibility of the disconnection duration can be verified. The equations/procedures applied for this verification can depend on the residual insulin and the amount of bolus in process.

For example, if there is no bolus in process and RI>0, at 406a, the following condition can be used for the feasibility test:

$$BGmax > CBG + BGei - RI * IS.$$

If the RI=0, then the test condition can be:

$$BGmax > CBG + BGei - 0.$$

If there is a bolus in the process (also referred to as a "bolus in progress"), at 406b, then the test condition can be: BGmax>CBG+BGei+REB*IS, wherein REB can relate to the portion of the bolus that was interrupted and not delivered. If the selected condition at 406a or 406b can evaluate to TRUE, then, at 407, the contemplated disconnection time can be allowed with no need for a bolus prior to the disconnection (i.e. disconnection bolus, DB). Otherwise, a disconnection bolus can be determined at 408, depending on the amount of residual insulin, at 408a, or the existence of a bolus in process, at 408b.

At 408a, if there is no bolus in process and there is residual insulin then the following equation can determine the amount of the DB:

$$DB = ((CBG - BGmax + BGei)/IS) - RI$$

If there is no bolus in process and no residual insulin then the following equation can determine the amount of the DB:

$$DB = ((CBG - BGmax + BGei)/IS) - 0$$

At 408b, if there is a bolus in process then the DB can be determined as follows:

$$DB = ((CBG - BGmax + BGei)/IS) + REB$$

Another feasibility test, at 409, can then be conducted automatically. The following condition can be used:

$$BGmin < CBG - DB * IS$$

If the feasibility test evaluates to TRUE, at 410, the contemplated disconnection time can be allowed with a need for a bolus prior to the disconnection (i.e. disconnection bolus, DB). Otherwise, if the contemplated disconnection time is still too long, despite lowering the BG to BGmin, then, at 411a or 411b, depending on whether there is a bolus in process, the time limit can be offered. The time limit can be calculated differently based on various options.

For example, if there is no bolus in process and there is residual insulin, see 411a, then Tmax can be calculated as Tmax=(BGmax−BGmin+RI*IS)/(basal*IS) and the disconnection bolus is than equivalent to $((CBG-BG_{min})/IS)-RI$. If there is no bolus in process and there is no residual insulin then Tmax can be calculated as Tmax=(BGmax−BGmin)/(basal*IS). The disconnection bolus is than equivalent to $((CBG-BG_{min})/IS)$. If there is a bolus in process, see 411b, then Tmax can be calculated as Tmax=(BGmax−BGmin−REB*IS)/(basal*IS) and the disconnection bolus is than equivalent to $((CBG-BG_{min})/IS)+REB$.

After reconnection of the pump, at 412,413 or 414, the reconnection bolus (RB, RB' or RB") can be administered to bring the user back to target blood glucose levels (TBG). If the user's disconnection time was limited by the device, at 414, the reconnection bolus can be administered automatically (with or without the user intervention) according to the following equation: (BGmin+basal*Tmax*IS−TBG)/IS. This equation can also be presented in the following form: RB=(BGmax−TBG)/IS, because BGmax can be calculated as BGmax=BGmin+basal*Tmax*IS.

In cases where residual insulin (RI) exists, the RI can be subtracted from the RB calculated above, see 414a. In cases where a bolus in process was halted due to disconnection, the REB should be added to the RB calculated above, see 414b. Any combination of the cases noted above can be calculated by subtraction and/or addition of RI and/or REB respectively.

If the user's disconnection time was not limited by the device, and there was no need for a disconnection bolus, at 412, the correction bolus can be administered automatically according to the following fundamental equation: (CBG+basal*T*IS−TBG)/IS. This equation can be extended in various cases based on several options. For example, if the basal rate is inconstant the reconnection bolus (RB) can be calculated as follows: RB=(CBG+Σ$basal_x * t_x$*IS−TBG)/IS. An inconstant basal profile is composed of x segments of time (the $x^{th}$ segment is designated as $time_x$) while during each time segment, a constant basal rate is delivered (the basal rate delivered during the segment $time_x$ will be designated as $basal_x$).

In some implementations, a basal profile can be composed of two time segments: a first segment which lasts 3 hours ($time_1=3$) and a second segment which lasts 2 hours ($time_2=2$). During the first time segment a constant basal rate of 1 Unit/hour is delivered (i.e. $basal_1=2$) and during the second time second a constant basal rate of 0.5 Unit/hour is delivered ($basal_2=0.5$). Hence, the inconstant basal profile can be presented as $\Sigma(basal_x*t_x)$ where the summation index "x" starts at 1 over all integers and stops at 2, i.e. taking into consideration all the segments composing the basal profile yielding with $\Sigma(basal_x*t_x)=2*3+0.5*2=7$ Units. In this example, the rest of parameters are constant, however if for example IS is inconstant, it could be integrated as well to the summation, e,g, $RB=(CBG+\Sigma((basal_x*t_x*IS_x)-TBG)/IS_x)$.

At 412a, if no bolus in process and RI>0, then RB can be calculated as follows: $RB=(CBG+basal*T*IS-TBG)/IS-\Sigma RI$ for a constant basal rate where $\Sigma RI$ represents the current amount residual insulin. For an inconstant basal rate the correction bolus can be calculated as follows: $RB=(CBG+\Sigma basal_x*t_x*IS-TBG)/IS-\Sigma RI$.

At 412b, if a bolus in process, RB can be calculated as $RB=(CBG+basal*T*IS-TBG)/IS+REB$ for a constant basal rate. For an inconstant basal rate the correction bolus can be calculated as follows: $RB=(CBG+\Sigma basal_x*t_x*IS-TBG)/IS+REB$.

If the user's disconnection time was not limited by the device, and there was a need for a disconnection bolus, a correction bolus may automatically be administered (numeral 413).

If no bolus in process and no RI, then, for a constant basal rate the RB can be calculated as follows: $RB=(CBG-DB*IS+basal*T*IS-TBG)/IS$. For an inconstant basal rate the correction bolus is as follows: $RB=(CBG-DB*IS+\Sigma basal_x*t_x*IS-TBG)/IS$.

At 413a, if no bolus in process and RI>0, the RB can be calculated as follows: $RB=(CBG-DB*IS+basal*T*IS-TBG)/IS-\Sigma RI$ for a constant basal rate. For an inconstant basal rate the correction bolus can be calculated as follows: $RB=(CBG-DB*IS+\Sigma basal_x*t_x*IS-TBG)/IS-\Sigma RI$.

At 413b, if a bolus in process, then, for a constant basal rate, the RB can be calculated as follows: $RB=(CBG-DB*IS+basal*T*IS-TBG)/IS+RB$. For an inconstant basal rate the correction bolus can be calculated as follows: $RB=(CBG-DB*IS+\Sigma basal_x*t_x*IS-TBG)/IS+REB$.

The user can also check his/her reconnection blood glucose level (RBG), and a correction bolus may be administered according to the following equation: $CB=(RBG-TBG)/IS$. If at steps 408a, 408b, 411a or 411b a negative DB is calculated, then, in some examples, it may be rounded to 0, i.e. no need for a disconnection bolus.

The user can also be advised to avoid food intake during the time disconnected from the infusion device.

Figure 5:
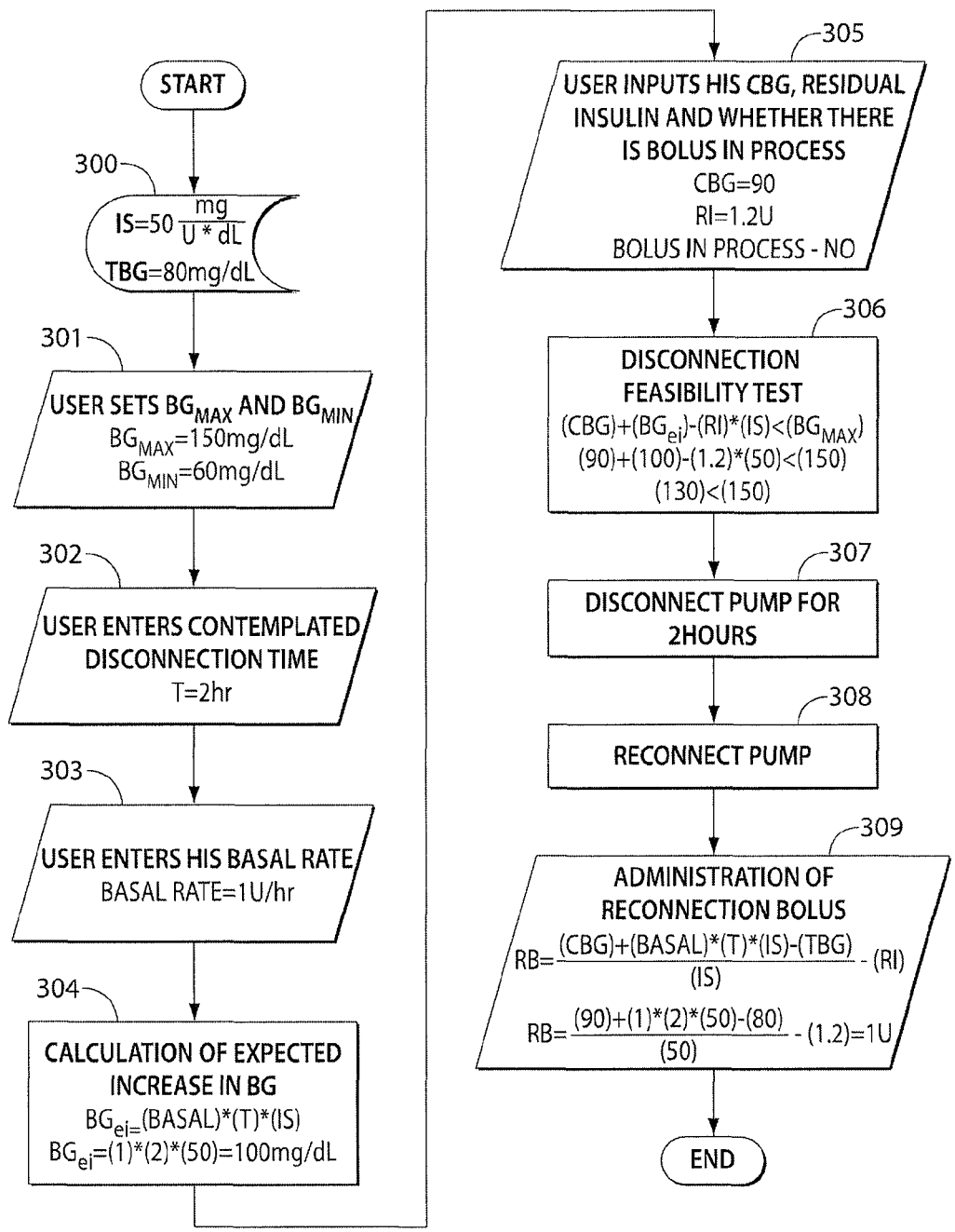
FIG. 5 is a block diagram illustrating one example of the controlled disconnection method.

FIG. 5 illustrates one example of the controlled disconnection method in which the user can be allowed to disconnect for the contemplated disconnection time without any need for the disconnection bolus. In the given example, there is no bolus in process and there is residual insulin left in the body from previous boluses.

At 300, the patient's insulin sensitivity (IS), and target blood glucose (TBG) can be determined. At 301, the user can set the BGmin and BGmax to 60 mg/dL and 150 mg/dL respectively. At 302, the user can input the contemplated disconnection time of 2 hours. At 303, the user can input the basal rate that would have been suitable had there been no disconnection of 1 U/h. At 304, the expected increase in BG during the contemplated disconnection time can be calculated to be 100 mg/dL. At 305, the current BG value of 90 mg/dL, the residual insulin value of 1.2 U and the existence of bolus in process can either be determined automatically or entered by the user. At 306, the initial feasibility test can determine that the user's expected BG at the end of the contemplated disconnection time is lower than BGmax. As a result, the user can be allowed to disconnect without any infusion of a disconnection bolus. At 307, the user disconnects the infusion device, and after 2 hours reconnects at 308. At 309, a reconnection bolus of 1 U of insulin can be administered to bring the user to the target BG level.

Figure 6:
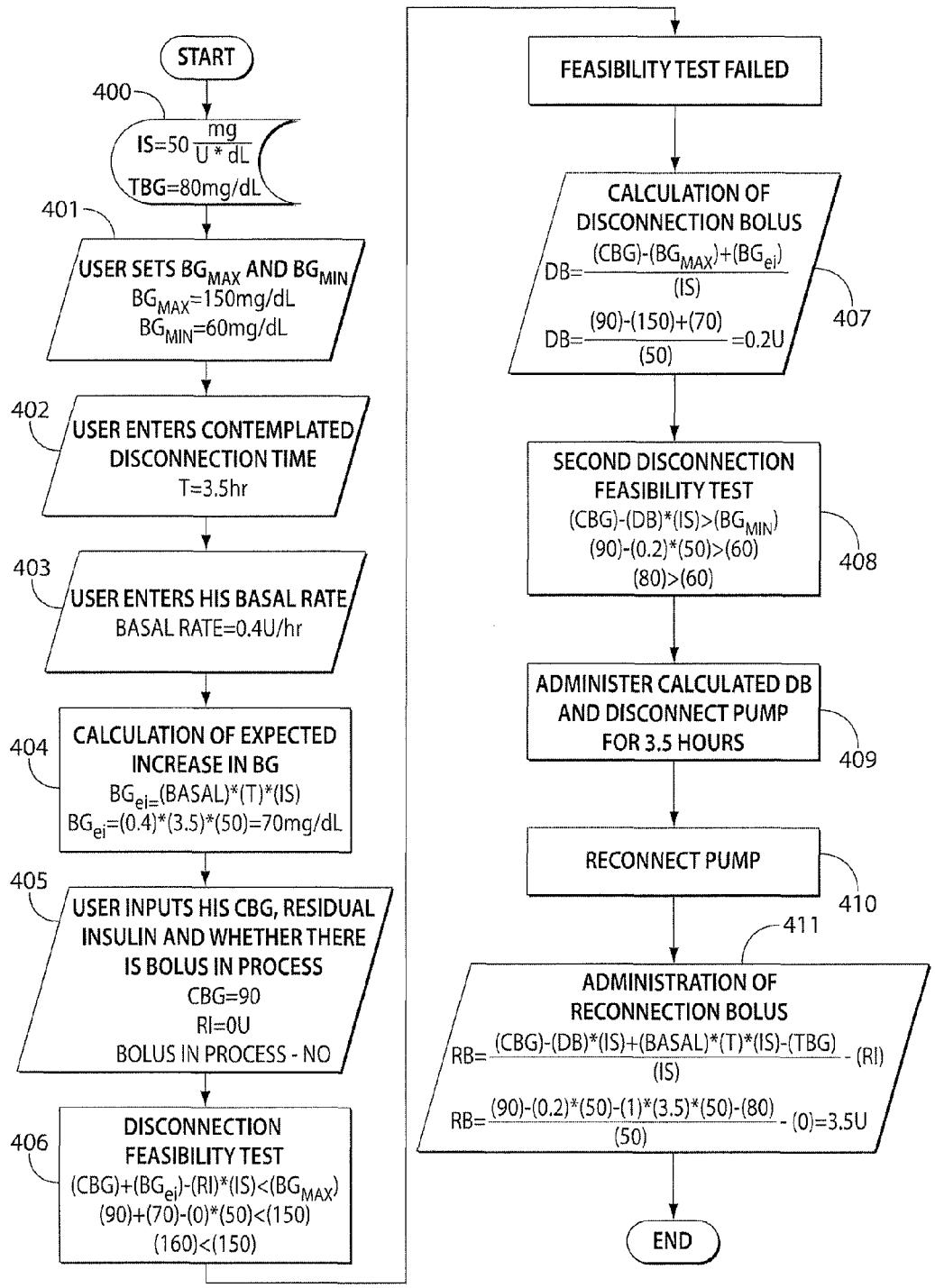
FIG. 6 is a block diagram illustrating another example of the controlled disconnection method.

FIG. 6 illustrates another example of the controlled disconnection method in which the user is allowed to disconnect for the contemplated disconnection time with a necessity for a disconnection bolus. In the given example, it can be determined that there is no bolus in process and there is no residual insulin left in the body from the previous boluses.

At 400, the patient's insulin sensitivity (IS), and the target blood glucose (TBG) can be determined. At 401, the user can set a BGmin and BGmax to 60 and 150 mg/dL respectively. At 402, the user can input a contemplated disconnection time of 3.5 hours. At 403, the user can input a basal rate that would have been suitable had there been no disconnection of 0.4 U/h. At 404, the expected increase in BG during the contemplated disconnection time can be calculated to be 70 mg/dL. At 405, the user can input the current BG, which is 90 mg/dL, that there is no residual insulin and that there is no bolus in process. Alternatively, all these 3 values can be determined automatically.

At 406, according to the initial feasibility test, the user's expected BG at the end of the contemplated disconnection time can be determined to be higher than BGmax. As a result, the user may not be allowed to disconnect and there is a need for a disconnection bolus.

At 407, the user can administer a disconnection bolus (DB) of 0.2 U. At 408, according to the second feasibility test, the user's expected BG after DB administration can be determined to be higher than BGmin. As a result, the user can disconnect and there is a need to limit the disconnection time. At 409, the user can disconnect the infusion device and, at 410, after 3.5 hours reconnect. At 411, a reconnection bolus of 3.5 U of insulin can then be administered to bring the user to the target BG level.

Figures 1, 7:
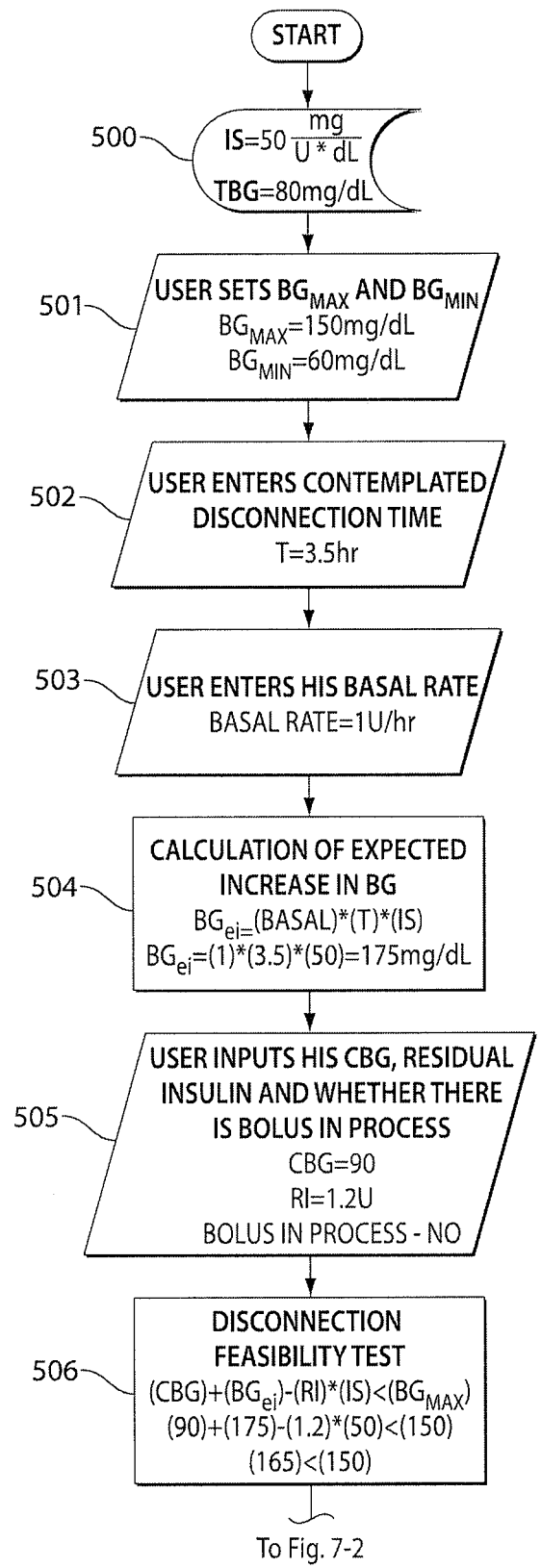
FIG. 7 is a block diagram illustrating yet another example of the controlled disconnection method.
Figures 2, 7:
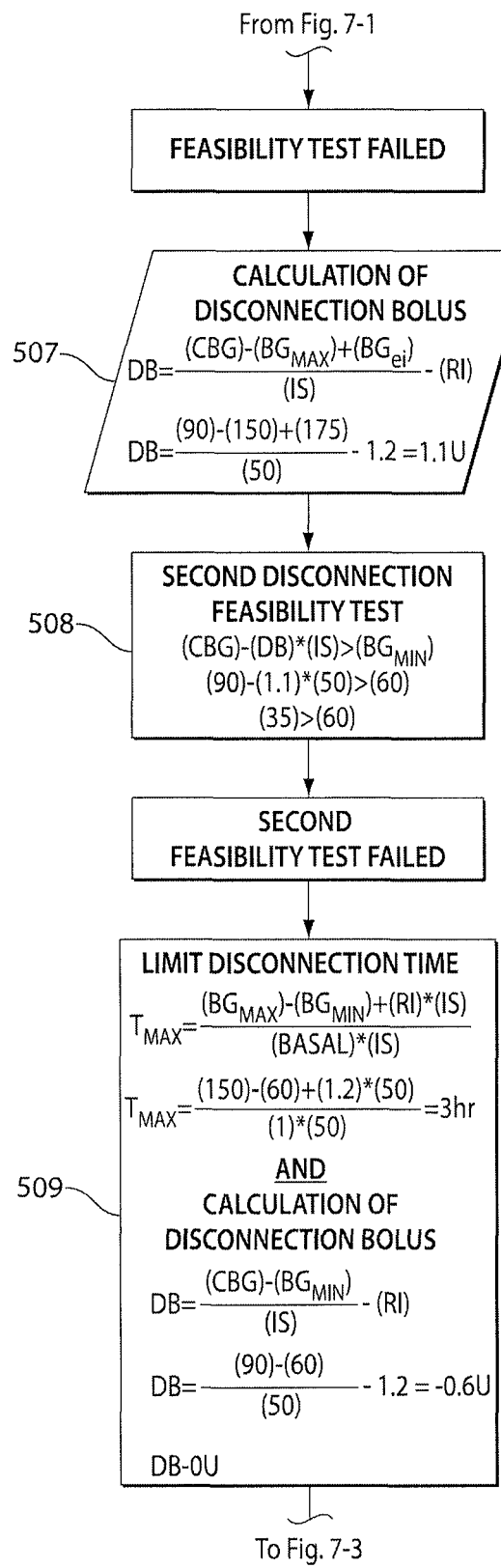
Figures 3, 7:
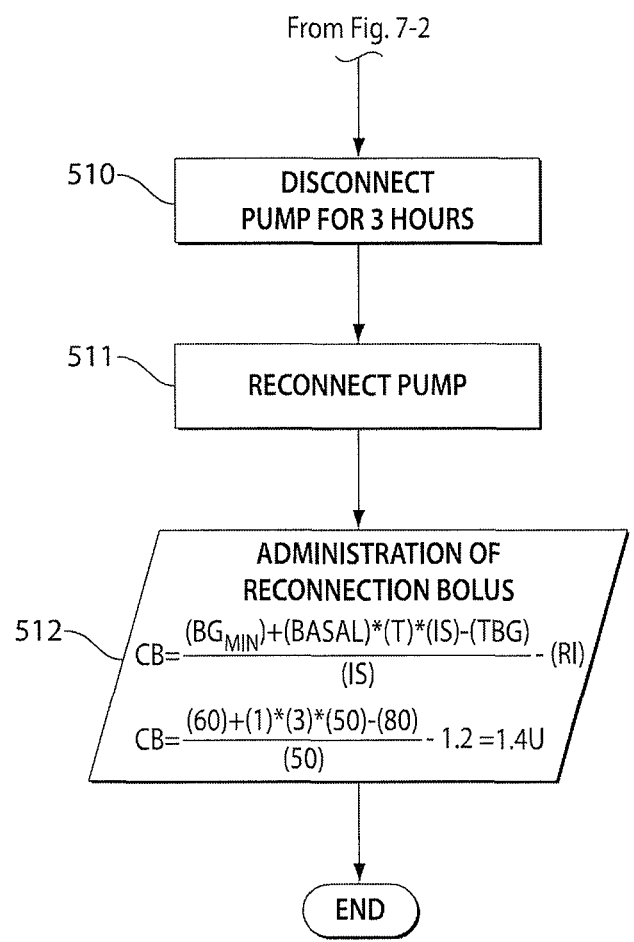

FIG. 7 illustrates a block diagram representing an example of the controlled disconnection method in which there is a need for a disconnection bolus and the user is not allowed to disconnect for the contemplated disconnection time. In the given example, there is no bolus in process and there is residual insulin left in the body from previous boluses.

At 500, the patient's insulin sensitivity (IS), and the target blood glucose (TBG) can be determined. At 501, the user can set a BGmin and BGmax of 60 and 150 mg/dL respectively. At 502, the user can input a contemplated disconnection time of 3.5 hours. At 503, the user can input a basal rate that would have been suitable had there been no disconnection of 1 U/h. At 504, the expected increase in BG during the contemplated disconnection time can be calculated to be 175 mg/dL. At 505, the user can input the current BG which is 90 mg/dL, there is residual insulin and there is no bolus in process.

At 506, according to the initial feasibility test, the user's expected BG at the end of the contemplated disconnection time is higher than BGmax. Consequently, the user may not be allowed to disconnect without administering the disconnection bolus. At 507, a disconnection bolus (DB) of 1.1 U is calculated. At 508, according to the second feasibility test, the user's expected BG after theoretical DB administration can be determined to be lower than BGmin. Consequently, at 509, a need to limit the disconnection time to 3 hours can be determined. A new DB can be calculated according to ((CBG-$BG_{min}$)/IS)−RI=−0.6. A negative DB is rounded to zero. At 510, the user can disconnect the infusion device, and, at 511, after 3 hours reconnect. At 512, a reconnection bolus of 1.4 U of insulin can then be administered to bring the user to target BG level.

Figure 8A:
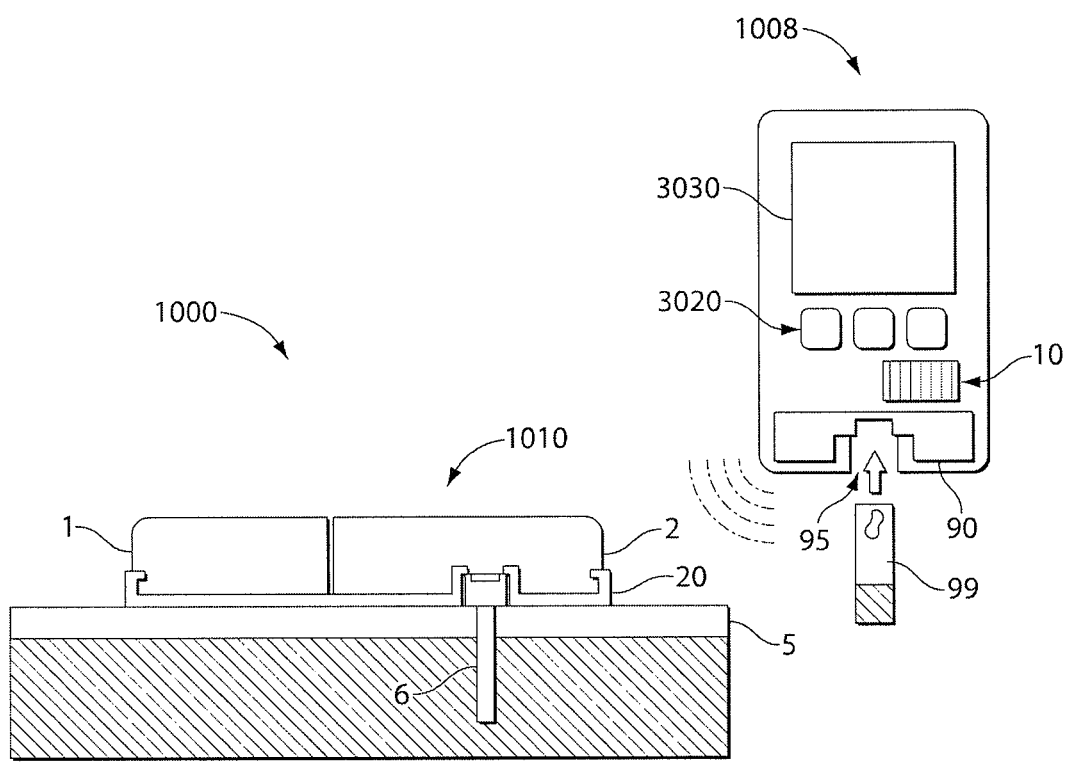
FIGS. 8a-c illustrate three configurations of an insulin infusion system comprising blood glucose monitor providing blood glucose (BG) readings for the controlled disconnection apparatus.
Figure 8B:
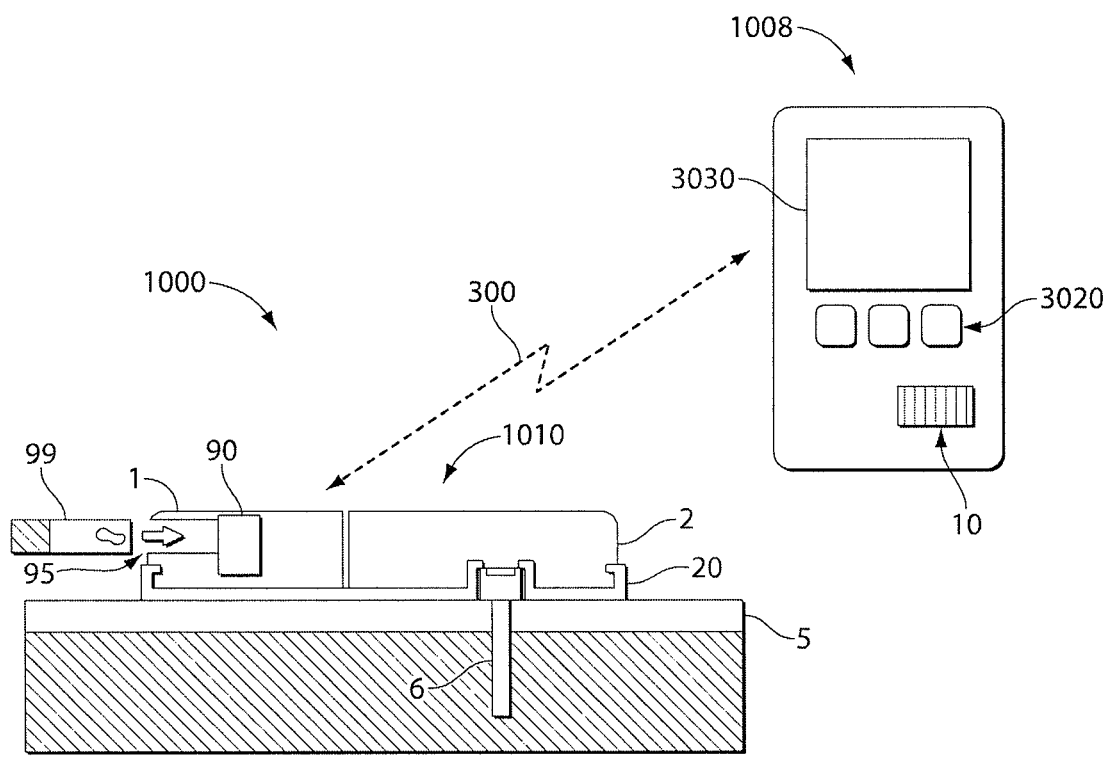
Figure 8C:
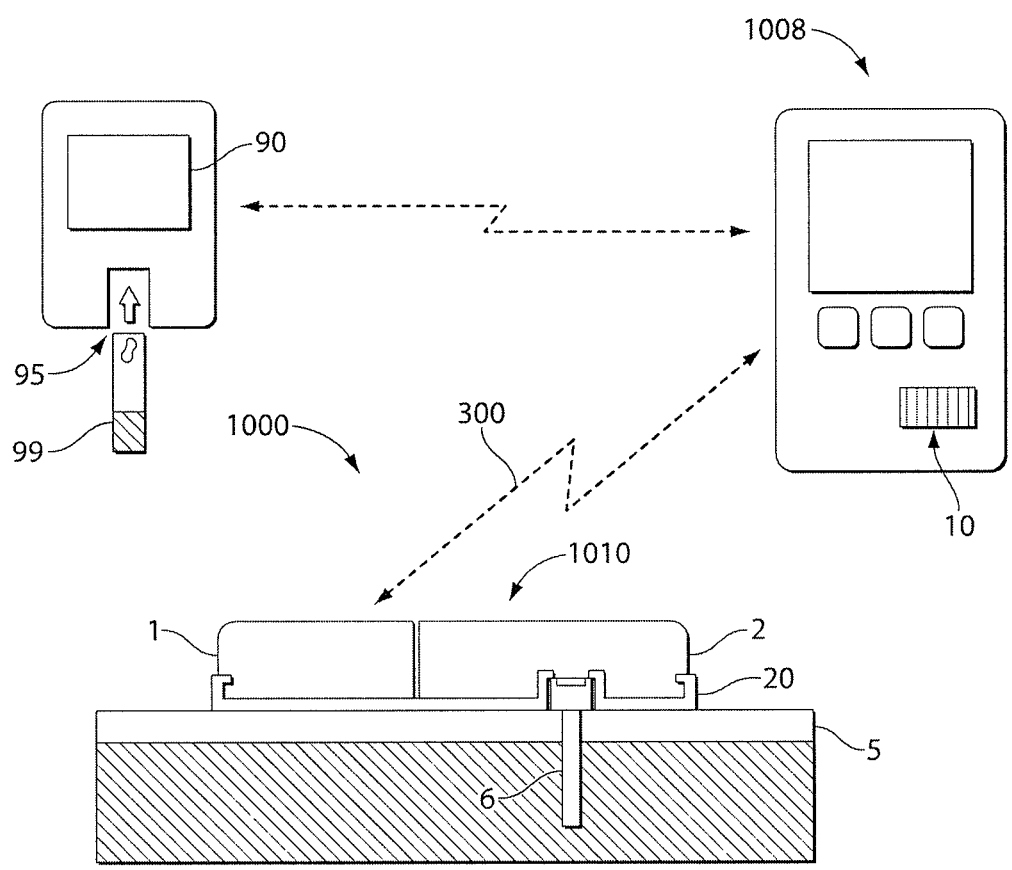

FIG. 8*a*-*c* illustrate three different implementations of the insulin infusion system, each includes a glucometer 90 to be used as blood glucose (BG) inputs for the controlled disconnection apparatus 10.

FIG. 8*a* illustrates one implementation of a glucose measurement device (glucometer) 90 located in the remote control unit 1008 of the device. In some implementations, the glucose measurement device can be incorporated in the remote control unit. In another implementation, the glucose measurement device can be incorporated into a separate skin-securable device. The glucose measurement device can also be incorporated, for example, into the same housing as the insulin infusion pump.

The glucometer 90 can comprise an opening 95 for receiving of a test strip 99. For example, the user can extract a blood sample from the body, place a blood drop on the test strip 99 and insert the strip 99 into the opening 95. The glucose readings can be displayed on the screen 3030 of the remote control unit 1008.

FIG. 8*b* shows another implementation of the glucometer 90 located in the reusable part 1 of the patch unit 1010. A communication channel 300 between the glucometer 90 residing in the patch unit 1010 and the controlled disconnection apparatus 10 residing in the remote control unit 1008 can be maintained, for example, for programming, data handling, and user input purposes.

FIG. 8*c* shows an implementation in which glucose readings are directly or remotely received from an independent glucometer 90.

Various implementations of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

Although a few variations have been described in detail above, other modifications are possible. For example, the logic flow depicted in the accompanying figures and described herein does not require the particular order shown, or sequential order, to achieve desirable results. Other implementations may be within the scope of the following claims.

What is claimed is:

1. A method for controlled disconnection of a therapeutic treatment device comprising:
   providing a processor for at least one of programming and operating the treatment device;
   receiving a current amount of glucose in a user's body;
   automatically determining, by the processor, an amount of insulin for dispensing into the user's body as a function of the current amount of glucose and a contemplated disconnection time; and
   upon the processor determining an amount of insulin for dispensing, initiating dispensing of the determined amount of insulin into the user's body without additional user input of a percentage of the determined amount of insulin for dispensing into the user's body.

2. The method of claim 1, wherein the amount of insulin is determined based on at least one of: an insulin sensitivity, a target glucose level, an amount of residual insulin, the maximum glucose amount and the minimum glucose amount, a portion of a bolus in progress.

3. The method of claim 1, further comprising continuously monitoring the current amount of glucose in the user's body.

4. The method of claim 1, wherein the contemplated disconnection time is configurable by the user.

5. The method of claim 1, wherein the dispensing the determined amount of insulin into the user is performed prior to disconnection and/or after reconnection of the therapeutic treatment device.

6. The method of claim 1, wherein the dispensing of the determined amount of insulin into the user's body comprises:
   dispensing a first portion of a bolus amount into the user's body prior to disconnection of the therapeutic treatment device; and dispensing a second portion of the bolus amount into the user's body after reconnection of the therapeutic treatment device.

7. The method of claim 1, wherein the amount of insulin for dispensing into the user's body is further determined in correspondence with an amount of basal insulin.

8. The method of claim 1, further comprising alerting the user to limit the contemplated disconnection time.

9. The method of claim 1, further comprising measuring blood glucose using a glucose measuring device that is accommodated in at least one of: a remote control and a dispensing unit of the therapeutic treatment device.

10. The method of claim 1, wherein the therapeutic treatment device comprises an insulin dispensing unit to dispense the determined amount of insulin to the user's body.

11. The method of claim 10, wherein the insulin dispensing unit is skin adherable.

12. The method of claim 10, wherein the insulin dispensing unit is connectable and disconnectable to and from the body of user.

13. The method of claim 12, wherein the therapeutic treatment device further comprises a skin securable cradle enabling repeated connection and disconnection of the insulin dispensing unit to and from the body of user.

14. The method of claim 1, further comprising receiving at least one of a maximum and a minimum tolerable blood glucose level for the user, wherein the amount of insulin for dispensing into the user's body is determined as a function of the current amount of glucose, the contemplated disconnection time, and the at least one of the maximum and minimum tolerable blood glucose level.

15. The method of claim 14, wherein the maximum tolerable blood glucose level is determined for preventing hyperglycemia of the user, and the minimum tolerable blood glucose level is determined for preventing hypoglycemia of the user.

16. The method of claim 1, further comprising determining, by the processor, the contemplated disconnection time based on the current amount of glucose.

17. The method of claim 1, wherein prior to determining the amount of insulin for dispensing, the method further comprises receiving, by the processor, a plurality of contemplated disconnection times, wherein the amount of insulin is determined by the processor for each contemplated disconnection times as a function of the current amount of glucose and each respective contemplated disconnection time.

18. The method of claim 1, further comprising:
receiving a contemplated disconnection time; and
validating, by the processor, the contemplated disconnection time as a function of the current amount of blood glucose,
wherein the determined amount of insulin for dispensing into the user's body corresponds to the validated contemplated disconnection time.

19. The method of claim 18, wherein validating the contemplated disconnection time comprises calculating the expected blood glucose change during the contemplated disconnection time.

20. The method of claim 19, wherein upon the expected blood glucose rising during the contemplated disconnection time to a level which is smaller than a maximum tolerable blood glucose level, therein the therapeutic device disconnection is enabled.

21. The method of claim 19, wherein upon the expected blood glucose rising during the contemplated disconnection time to a level which is larger than the maximum tolerable blood glucose level, therein determining the amount of insulin for dispensing into the user's body further comprises calculating the expected blood glucose decrease due to delivery of the determined amount.

22. The method of claim 21, wherein:
upon the expected blood glucose decreasing to a value above a minimum tolerable blood glucose level, therein the determined amount of insulin is delivered prior to disconnection;
and
upon the expected blood glucose decreasing to a value below the minimum tolerable blood glucose level, therein the contemplated disconnection time is limited by the processor and the determined amount of insulin is adjusted in accordance with a new contemplated disconnection time.

23. The method of claim 1, further comprising alarming the user when the contemplated disconnection time is approaching or has lapsed.

24. The method of claim 1, wherein initiation of the determined amount of insulin into the user's body is performed without any additional user input.

25. A method for controlled disconnection of a therapeutic treatment device comprising:
providing a processor for at least one of programming and operating the treatment device;
receiving a current amount of glucose in a user's body;
receiving a contemplated disconnection time;
validating, by the processor, the contemplated disconnection time as a function of the current amount of blood glucose;
automatically determining, by the processor, an amount of insulin for dispensing into the user's body which corresponds to the validated contemplated disconnection time; and
upon the processor determining an amount of insulin for dispensing, initiating dispensing of the determined amount of insulin into the user's body.

26. A method for controlled disconnection of a therapeutic treatment device comprising:
providing a processor for at least one of programming and operating the treatment device;
receiving a current amount of glucose in a user's body;
receiving a contemplated disconnection time;
validating, by the processor, the contemplated disconnection time as a function of the current amount of blood glucose;
automatically determining, by the processor, an amount of insulin for dispensing into the user's body which corresponds to the validated contemplated disconnection time; and
upon the processor determining an amount of insulin for dispensing, initiating dispensing of the determined amount of insulin into the user's body without additional user input of a percentage of the determined amount of insulin for dispensing into the user's body.

27. The method of claim 26, wherein initiation of the determined amount of insulin into the user's body is performed without any additional user input.

28. A method for controlled disconnection of a therapeutic treatment device comprising:
providing a processor for at least one of programming and operating the treatment device;
receiving a current amount of glucose in a user's body;
receiving at least one of a maximum and a minimum tolerable blood glucose level for the user,
automatically determining, by the processor, an amount of insulin for dispensing into the user's body as a function of the current amount of glucose, a contemplated disconnection time and at least one of a maximum and a minimum tolerable blood glucose level of the user; and upon the processor determining an amount of insulin for dispensing, initiating dispensing of the determined amount of insulin into the user's body.

* * * * *